(12) United States Patent
Wolfe

(10) Patent No.: US 9,955,697 B2
(45) Date of Patent: May 1, 2018

(54) WEED CONTROL AND FERTILIZER

(71) Applicant: One Earth Organics, LLC, Boulder, CO (US)

(72) Inventor: Bradley T. Wolfe, Boulder, CO (US)

(73) Assignee: One Earth Organics, LLC, Boulder, CO (US)

( * ) Notice: Subject to any disclaimer, the term of this patent is extended or adjusted under 35 U.S.C. 154(b) by 0 days. days.

(21) Appl. No.: 15/085,061

(22) Filed: Mar. 30, 2016

(65) Prior Publication Data

US 2017/0280723 A1 Oct. 5, 2017

(51) Int. Cl.
| | | |
|---|---|---|
| *A01N 55/02* | (2006.01) | |
| *A01N 61/00* | (2006.01) | |
| *C05C 9/00* | (2006.01) | |
| *C05D 9/00* | (2006.01) | |
| *C05D 9/02* | (2006.01) | |

(52) U.S. Cl.
CPC ............ *A01N 55/02* (2013.01); *A01N 61/00* (2013.01); *C05C 9/00* (2013.01); *C05D 9/00* (2013.01); *C05D 9/02* (2013.01)

(58) Field of Classification Search
None
See application file for complete search history.

(56) References Cited

U.S. PATENT DOCUMENTS

| | | | | |
|---|---|---|---|---|
| 4,519,845 A | * | 5/1985 | Ou ..................... | C13B 20/148 127/46.2 |
| 6,241,795 B1 | | 6/2001 | Svec et al. | |
| 6,271,177 B1 | * | 8/2001 | Hudetz ................. | A01N 25/32 504/124 |
| 7,776,124 B2 | | 8/2010 | Binder et al. | |
| 7,947,104 B2 | | 5/2011 | Burnham et al. | |
| 8,110,017 B2 | | 2/2012 | Wells | |
| 8,557,013 B2 | | 10/2013 | Burnham et al. | |
| 8,920,733 B2 | | 12/2014 | Burnham et al. | |
| 8,992,654 B2 | | 3/2015 | Dahms et al. | |
| 2007/0173409 A1 | | 7/2007 | Freire et al. | |
| 2009/0004167 A1 | * | 1/2009 | Boulos .................. | A01N 59/00 424/94.1 |
| 2009/0229331 A1 | | 9/2009 | Wells | |
| 2010/0154498 A1 | | 6/2010 | Valencia | |
| 2011/0154873 A1 | | 6/2011 | Burnham et al. | |
| 2011/0265532 A1 | | 11/2011 | Burnham et al. | |
| 2012/0010078 A1 | | 1/2012 | Garcia-Mina et al. | |
| 2012/0090365 A1 | * | 4/2012 | Ersek ..................... | C05F 9/04 71/7 |
| 2012/0247164 A1 | | 10/2012 | Dahms et al. | |
| 2013/0160506 A1 | * | 6/2013 | Lynch .................... | C05C 3/005 71/25 |
| 2014/0137614 A1 | | 5/2014 | Burnham et al. | |
| 2015/0080216 A1 | * | 3/2015 | Wikeley ................ | A01N 43/08 504/136 |
| 2015/0101374 A1 | | 4/2015 | Burnham et al. | |
| 2015/0191399 A1 | | 7/2015 | Dahms et al. | |

FOREIGN PATENT DOCUMENTS

CA 2926037 9/2017

\* cited by examiner

*Primary Examiner* — Mina Haghighatian
*Assistant Examiner* — Luke E Karpinski
(74) *Attorney, Agent, or Firm* — Bethany R. Roahrig; Barbara Campbell; Cochran Freund & Young LLC

(57) ABSTRACT

A composition for weed control and fertilizer comprising an effective amount of iron hydroxyl ethylenediaminetriacetic acid, micromate, feed grade urea, a natural-based wetting agent, molasses desurgarized solubles, and water, and may further comprise glycerin, are provided. Methods for weed control and fertilization of plants comprising the steps of providing a composition comprising an effective amount of iron hydroxyl ethylenediaminetriacetic acid, micromate, feed grade urea, natural-based wetting agent, and molasses desurgarized solubles, and applying an effective amount of the composition to soil or a plant or a weed, are also provided.

10 Claims, 8 Drawing Sheets
(7 of 8 Drawing Sheet(s) Filed in Color)

WEED CONTROL AND FERTILIZER

BACKGROUND

Soil contains many of the essential elements needed for plant growth. However, to achieve maximum growth and yield fertilizers and various forms of weed control are often employed to enrich the soil and supplement nutrients that are needed for optimum plant growth.

The foregoing examples of related art and limitations related therewith are intended to be illustrative and not exclusive, and they do not imply any limitations on the inventions described herein. Other limitations of the related art will become apparent to those skilled in the art upon a reading of the specification and a study of the drawings.

SUMMARY

The following embodiments and aspects thereof are described and illustrated in conjunction with systems, tools and methods, which are meant to be exemplary and illustrative, not limiting in scope. In various embodiments, one or more of the above-described problems have been reduced or eliminated, while other embodiments are directed to other improvements.

One embodiment may comprise a composition for weed control and fertilizer comprising an effective amount of iron hydroxyl ethylenediaminetriacetic acid, micromate, feed grade urea, a natural-based wetting agent, molasses desurgarized solubles, and water, and may further comprise glycerin.

One embodiment may further comprise a method for weed control and fertilization of plants comprising the steps of providing a composition comprising an effective amount of iron hydroxyl ethylenediaminetriacetic acid, micromate, feed grade urea, a natural-based wetting agent, molasses desurgarized solubles and water, and applying an effective amount of the composition to soil, lawn, or a cultivated area.

One embodiment may further comprise a kit for weed control and fertilizer comprising iron hydroxyl ethylenediaminetriacetic acid, borresol humate HA-1, chelated micronutrients, feed grade urea, a natural-based wetting agent, and molasses desurgarized solubles. The kit may further comprise glycerin.

In addition to the example, aspects and embodiments described above, further aspects and embodiments will become apparent by study of the following descriptions, any one or all of which are within the invention. The summary above is a list of example implementations, not a limiting statement of the scope of the invention.

BRIEF DESCRIPTION OF THE DRAWINGS

The accompanying figures, which are incorporated herein and form a part of the specification, illustrate some, but not the only or exclusive, example embodiments and/or features. It is intended that the embodiments and figures disclosed herein are to be considered illustrative rather than limiting.

The patent or application file may contain one or more drawings executed in color and/or one or more photographs. Copies of this patent or patent application publication with color drawing(s) and/or photograph(s) will be provided by the Patent Office upon request and payment of the necessary fee.

DETAILED DESCRIPTION

Figure 1:
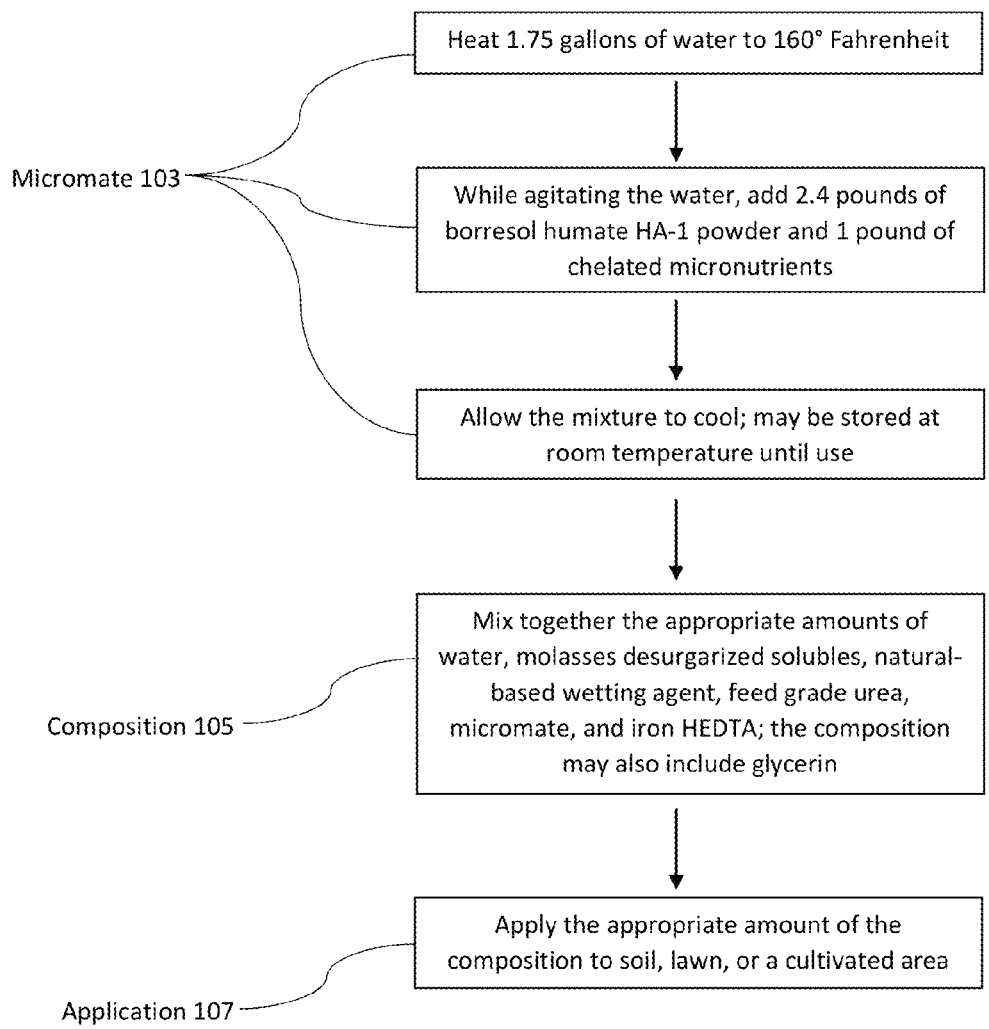
FIG. 1 is a flow diagram of how to make and use the composition of the present disclosure.

The present invention relates broadly to a formulation for weed control and fertilizer. The formulations comprise iron hydroxyl ethylenediaminetriacetic acid (iron HEDTA), micromate, feed grade urea, a natural-based wetting agent, molasses desurgarized solubles (MDS), and water, and may also contain glycerin. The composition is thoroughly mixed together to form a solution that is then applied to soil, lawn, or a cultivated area in order to kill weeds and fertilize plants. The solution may be applied, for example, up to 8 times per year in tropical climates and those with mild winters, or may be applied 6 to 8 weeks apart for example, in temperate climates. In the case of rain following treatment, the solution may be re-applied one week later to ensure adequate results.

As will be understood by one skilled in the art, the formulation of the present disclosure may comprise combinations including but not limited to iron HEDTA, micromate, feed grade urea, a natural-based wetting agent, MDS, and water, and may further comprise glycerin.

Table 1 below shows approximate percentage range of the ingredients of the formulation as an embodiment of the present disclosure for the control of weeds and fertilization of plants. Column 1 shows a list of the ingredients of one or more embodiments of the composition of matter of the present disclosure. Column 2 shows the approximate percentage range of each ingredient of one or more embodiments of the present disclosure.

TABLE 1

| Ingredient | Approximate percentage range |
| --- | --- |
| Iron HEDTA | 6.6% to 6.8% |
| Micromate | 0.06% to 0.07% |
| Feed Grade Urea | 3.90% to 4.05%% (w/v) (kg/L) |
| A natural-based wetting agent | 0.04% to 0.05% |
| MDS | 6.5% to 10.5% |
| Glycerin | 0.06% to 0.07% |
| Water | Remaining percentage |

The application of the composition to soil, lawn, or a cultivated area in accordance with the teaching of the present disclosure kills weeds as well as fertilizes plants. The composition of the present disclosure is a post emergent weed control and fertilizer made from food grade ingredients that will kill most broadleaf weeds. The ingredients in the composition of the present disclosure function as catalysts for oxygen reduction, which causes the production of unstable and highly reactive oxygen radicals, such as hydroxyl radicals. This causes cellular damage within the weed, leading to plant death. The weeds cannot handle the nutrient overload because they metabolize them too quickly causing them to die, typically within 36 to 48 hours. Weed control rates range from between 60% to 90% reduction per application depending on the weed species and time of year.

Additionally, the composition of the present disclosure will fertilize the lawn and build beneficial microbial activity in soils. The composition of the present disclosure is considered non-toxic to pets, dogs, cats, people, and the environment.

Weeds

For purposes of the present disclosure, the term "weed" means a wild plant growing where it is not wanted and/or in competition with a cultivated area. Application of the composition of the present disclosure may kill the following weeds, but is not limited to: bindweed, black medic, broadleaf plantain, bull thistle, canada thistle, common chickweed, dandelion, false dandelion, mallow, narrow-leaved plantain, oxalis, Persian speedwell, prickly lettuce, prostrate spurge, purslane, redroot pigweed, slender speedwell, and white clover.

Table 2 below shows the weed and the approximate percent killed using the composition of the present disclosure. Column 1 lists the weed, column 2 shows the percentage of weeds killed, and column 3 shows the rating of weed control based on the percentage. The composition of the present disclosure works very well on controlling dandelions and often the control rates are up to 90% or greater when lawns are treated in the spring.

TABLE 2

| Weed | Percent killed | Rating |
| --- | --- | --- |
| Bindweed | 60% to 80% | Good |
| Black medic | 60% to 80% | Good |
| Broadleaf plantain | 80% to 90+% | Excellent |
| Bull thistle | 80% to 90+% | Excellent |
| Canada thistle | 80% to 90+% | Excellent |
| Dandelion | 90+% | Very Excellent, especially in the spring |
| False dandelion | 80% to 90+% | Excellent |
| Mallow | 60% to 80% | Good |
| Narrow-leaved plantain | 80% to 90+% | Excellent |
| Oxalis | 40% to 80% | Moderate |
| Persian speedwell | 60% to 80% | Good |
| Prickly Lettuce | 80% to 90+% | Excellent |
| Prostrate Spurge | 40% to 80% | Moderate |
| Purslane | 40% to 80% | Moderate |

TABLE 2-continued

| Weed | Percent killed | Rating |
| --- | --- | --- |
| Redroot Pigweed | 60% to 80% | Good |
| Slender speedwell | 60% to 80% | Good |
| White clover | 40% to 80% | Moderate |

Fertilization

For the purposes of the present disclosure, the term "fertilizer" means any material of natural or synthetic origin that is applied to soils or to plant tissues to supply one or more plant nutrients to the growth of plants.

Iron

In an embodiment of the present disclosure, a composition of matter for weed control and fertilization of plants is provided, where an aspect of the composition comprises iron. There is an iron hydroxyl ethylenediaminetriacetic acid (iron HEDTA) in the composition of the present disclosure, which can be purchased commercially, and it is a very strong chelating agent which means it is more available to the plant for uptake. Types of iron that may be bound to a chelating agent and used in the present disclosure include, but are not limited to, ferric nitrate and iron chloride.

Descriptive examples of the concentration of iron HEDTA of the formulation are shown in Tables 1, and 3-10 of the present disclosure. However, as will be apparent to one skilled in the art, these concentrations may encompass any percentage including but not limited to a range between 6.6% by volume and 6.8% by volume and all integers in between. Therefore, while these descriptive examples have 6.77%, 6.75%, 6.67%, or 6.70% by volume, it should be understood that these descriptions are applicable to any such concentration by volume including but not limited to volumes ranging between 6.6% by volume and 6.8% by volume and all integers in between, as will be understood by one skilled in the art, once they understand the principles of this invention. In some embodiments, the term "effective amount" of iron HEDTA may indicate an amount that is effective, when administered in a composition for weed control and plant fertilization as described herein.

Micromate

Micromate is a composition comprising borresol humate HA-1 (commercially available) and a chelated mix of micronutrients (commercially available, for example AXILO® Mix 5). The chelated mix of micronutrients may include, but is not limited to, for example, boron, copper, iron, magnesium, molybdenum, and zinc.

Humate is composed of organic matter that is millions of years old, that resulted from the decomposition of prehistoric plant and animal matter. Because it was once a living organism, it has many of the properties available to provide plants what they need for rapid and healthy growth. Humate also holds minerals and macro nutrients in available and soluble forms that can be assimilated and used by plants. Still further, humate provides direct plant stimulation by supplying a slow release of auxin, amino acids and organic phosphate, thus regulating hormone levels that tend to undergo rapid changes in stressed plants. In addition, humate serves as a substrate supporting the growth and proliferation of beneficial soil micro-organisms.

Humates also provide a number of physical benefits including increased water holding capacity of soil, increased aeration of soil, improved soil workability, improved seed bed, reduced soil erosion, and improved drought tolerance. Chemical benefits are also provided which include an increased percentage of total nitrogen in the soil, neutralized alkaline and acidic soils, maximized ion exchange capacity, maximized mineral uptake, and retention and release of fertilizer in root zones as needed. Still further, biological benefits are provided and include accelerated cell division thus stimulating plant growth, increased cell wall thickness thus extending shelf life, accelerated seed germination, increase of desirable micro-organisms in soil, increased vitamin content in plants, increased length wise root growth, maximized nutrient uptake, increased plant enzyme production, and enhanced photosynthesis.

Humate is primarily comprised of organic carbon in the form of humic acid and fulvic acid, but may also conatin ulmic acid and lignin, as well as many trace elements such as copper (Cu), iron (Fe), and zince (Zn). Humic acid is a naturally occurring dark brown substance found in association with fulvic acid. Fulvic acid is a naturally occurring yellow-brown product of microbial metabolism that can be extracted from sediment, and is a powerful organic electrolyte.

As shown in FIG. 1, to generate a 2 gallon mix of micromate 103, heat 1.75 gallons of water to approximately 160 degrees Fahrenheit, then while agitating the water mix in 2.4 pounds of borresol humate HA-1 powder and 1 pound of chelated micronutrients. The mixture is allowed to cool and may be stored at room temperature until use.

Descriptive examples of the concentration of micromate of the formulation are shown in Tables 1, and 3-10 of the present disclosure. However, as will be apparent to one skilled in the art, these concentrations may encompass any percentage including but not limited to a range between 0.06% by volume and 0.07% by volume and all integers in between. Therefore, while these descriptive examples have 0.068%, and 0.069% by volume, it should be understood that these descriptions are applicable to any such concentration by volume including but not limited to volumes ranging between 0.06% by volume and 0.07% by volume and all integers in between, as will be understood by one skilled in the art, once they understand the principles of this invention. In some embodiments, the term "effective amount" of micromate may indicate an amount that is effective, when administered in a composition for weed control and plant fertilization as described herein.

Urea

Urea serves an important role in the metabolism of nitrogen-containing compounds by animals, and is the main nitrogen-containing substance in the urine of mammals. Urea is a compound formed in the liver from ammonia produced by the deamination of amino acids and can be purchased commercially. It is the principal end product of protein catabolism and constitutes about one half of the total urinary solids. It is colorless, odorless solid, highly soluble in water, and practically non-toxic. Dissolved in water, it is neither acidic nor alkaline. The composition of the present disclosure uses feed grade urea. Its nitrogen becomes plant-available when converted to ammonium and then nitrate.

Descriptive examples of the concentration of urea of the formulation are shown in Tables 1, and 3-10 of the present disclosure. However, as will be apparent to one skilled in the art, these concentrations may encompass any percentage including but not limited to a range between 3.90% by weight to volume (w/v) and 4.05% by (w/v) and all integers in between. Therefore, while these descriptive examples have 3.97%, 3.98%, 4.00%, 4.01%, and 4.02% by weight to volume, it should be understood that these descriptions are applicable to any such concentration by weight to volume including but not limited to weight to volumes ranging between 3.90% by (w/v) and 4.05% by (w/v) and all integers in between, as will be understood by one skilled in the art, once they understand the principles of this invention. In some embodiments, the term "effective amount" of urea may indicate an amount that is effective, when administered in a composition for weed control and plant fertilization as described herein.

Natural-Based Wetting Agents

As used herein, "wetting agent" means any natural-based wetting agent, soil penetrant, and non-ionic surfactant derived from *Yucca schidigera*. Wetting agents can be commercially purchased, for example YUCCAH® and Therm X-70. Both of these products are derived from *Yucca schidigera*, a unique desert plant that produces natural surfactant compounds to help it manage water more efficiently. These surfactant compounds help improve the spreadability and soaking effect of water, even in very dry, water resistant soils. These are safe alternatives to chemical wetting agents. Other examples of wetting agents can include non-ionic surfactants derived from plants such as *Yucca schidigera*.

Descriptive examples of the concentration of natural-based wetting agents of the formulation are shown in Tables 1, and 3-10 of the present disclosure. However, as will be apparent to one skilled in the art, these concentrations may encompass any percentage including but not limited to a range between 0.04% by volume and 0.05% by volume and all integers in between. Therefore, while these descriptive examples have 0.046%, and 0.045% by volume, it should be understood that these descriptions are applicable to any such concentration by volume including but not limited to volumes ranging between 0.04% by volume and 0.05% by volume and all integers in between, as will be understood by one skilled in the art, once they understand the principles of this invention. In some embodiments, the term "effective amount" of a natural-based wetting agent may indicate an amount that is effective, when administered in a composition for weed control and plant fertilization as described herein.

Molasses Desugarized Solubles

Molasses Desugarized Solubles (MDS) is produced during the exclusion separation of sucrose from beet molasses and can be purchased commercially. In the process, sucrose is recovered for granulation and the greater part of the non-sugars of the original sugar beet molasses is separated into residual molasses and concentrated to produce MDS. Major components of MDS are: water, sugar, raffinose, betaine, amino acids, nitrogen compounds, inorganic salts and organic acid salts. These all occur naturally in sugar beets. MDS is a valuable animal feed additive that has many of the properties of molasses with more protein and minerals.

Descriptive examples of the concentration of molasses desugarized solubles (MDS) of the formulation are shown in Tables 1, and 3-10 of the present disclosure. However, as will be apparent to one skilled in the art, these concentrations may encompass any percentage including but not limited to a range between 6.5% by volume and 10.5% by volume and all integers in between. Therefore, while these descriptive examples have 6.69%, and 9.7% to 10.1% by volume, it should be understood that these descriptions are applicable to any such concentration by volume including but not limited to volumes ranging between 6.5% by volume and 10.5% by volume and all integers in between, as will be understood by one skilled in the art, once they understand the principles of this invention. In some embodiments, the term "effective amount" of MDS may indicate an amount that is effective, when administered in a composition for weed control and plant fertilization as described herein.

Glycerin

Descriptive examples of the concentration of glycerin of the formulation are shown in Tables 1, and 3-10 of the present disclosure. However, as will be apparent to one skilled in the art, these concentrations may encompass any percentage including, but not limited to, a range between 0.06% by volume and 0.07% by volume and all integers in between. Therefore, while these descriptive examples have 0.068%, and 0.069% by volume, it should be understood that these descriptions are applicable to any such concentration by volume including but not limited to volumes ranging between 0.06% by volume and 0.07% by volume and all integers in between, as will be understood by one skilled in the art, once they understand the principles of this invention. In some embodiments, the term "effective amount" of micromate may indicate an amount that is effective, when administered in a composition for weed control and plant fertilization as described herein.

Mode of Application

As will be understood by one skilled in the art, once they understand the principles of this invention, the ingredients described herein for the formulation of the present disclosure may be used in a variety of preparations and applications including but not limited to injection, surface broadcast, broadcast incorporated, band application, fertigation, foliar application, sidedress, topdress, and seed placement.

Injection is used to place liquids below the soil near plant roots. It reduces losses through precise application of nutrients. Surface broadcast is method whereby fertilizer is applied across an entire field. High capacity spreaders are used to spin dry fertilizer or spray liquid fertilizer on the soil surface or on a growing crop. It is fast and economical. Broadcast incorporated improves surface application by incorporating the fertilizer through plowing or disking. Band application is also known as starter application. In the band application method, fertilizer is applied in bands near developing roots. This can be done before or during seed planting. Fertigation is the distribution of water-soluble fertilizers through an irrigation system. Foliar application is a method whereby small amounts of fertilizer are applied by directing spraying the leaves. Sidedressing is when fertilizer is applied between rows of young plants to provide a boost during periods of growth. Topdressing is when fertilizer is spread on established fields (for example, grasses and legumes). Lastly, seed placement, also known as pop-up application is when a small amount of fertilizer is placed with seeds during planting.

EXAMPLES

The following examples are provided to illustrate further the various applications of the present invention and are not intended to limit the invention beyond the limitations set forth in the appended claims.

Example 1

The flow diagram shown in FIG. 1 outlines how to mix the composition of the present disclosure prior to use. To make two gallons of micromate 103, first heat 1.75 gallons of water to 160 degrees Fahrenheit, then while agitating the water add 2.4 pounds of borresol humate HA-1 powder and one pound of chelated micronutrients. Allow the mixture to cool prior to use in the composition of the present disclosure. Unused micromate may stored at room temperature. As will be understood by one skilled in the art, different amounts of micromate may be generated by altering the measurements of ingredients listed above in step 103. For example, 1 gallon of micromate may be generated by heating 0.875 gallons of water and adding 1.2 pounds of borresol humate HA-1 and 0.5 pound of chelated micronutrients.

To prepare the composition of the present disclosure, mix together the appropriate amounts of water, molasses desurgarized solubles, natural-based wetting agent, feed grade urea, micromate, and iron HEDTA 105. The composition may also include glycerin. Example amounts of the ingredients listed in step 105 are shown in Table 1 above and Tables 3-10 below. As shown in step 107, apply the appropriate amount of the composition to soil, lawn, or a cultivated area. Effective amounts of composition per square foot of area are shown in Tables 3-10 below. Application methods include, but are not limited to, injection, surface broadcast, broadcast incorporated, band application, fertigation, foliar application, sidedress, topdress, and seed placement.

Example 2

While other commercially available products may be used in the composition of the present disclosure, the natural-based wetting agent used in Tables 3-10 below was YUC-CAH®, and the chelated mix of micronutrients used in Tables 3-10 below was AXILO® Mix 5.

In Table 3 below different measurements of the ingredients are provided to treat from 250 square feet to 9,000 square feet (SQ), column one. The total volume is shown in three units of measurement: Liters (L) (column 2), ounces (oz) (column 3) and gallons (gal) (column 4). Columns 5 through 8 show the amount of water and MDS in two units of measurement, gallons and ounces. In column 9, the amount of natural-based wetting agent (WA) is shown in ounces. In columns 10 and 11, the amount of feed grade urea is shown in pounds (lbs) and kilograms (kg), respectively. In column 12, the amount of micromate (MT) is shown in ounces. In column 13, the amount of glycerin (GN) is shown in ounces. Lastly, in column 14, the amount of iron HEDTA is shown in ounces.

For example, row 3 shows the amount of each ingredient used as well as the total volume used to treat 250 square feet. The total volume/square foot equates to between 0.3 ounces and 0.4 ounces per square foot. The final composition may be applied by any of the methods described above directly to the soil, lawn, or a cultivated area, for example.

TABLE 3

| | Total Volume | | | H₂O | | MDS | | WA | Urea | | MT | GN | Iron |
|---|---|---|---|---|---|---|---|---|---|---|---|---|---|
| SQ | L | oz | gal | gal | oz | gal | oz | oz | lbs | kg | oz | oz | oz |
| 250 | 2.87 | 97.09 | 0.76 | 0.65 | 83.11 | 0.05 | 6.5 | 0.04 | 0.25 | 0.11 | 0.07 | 0.07 | 6.50 |
| 500 | 5.74 | 194.19 | 1.52 | 1.30 | 166.22 | 0.10 | 13 | 0.09 | 0.50 | 0.23 | 0.13 | 0.13 | 13.00 |
| 750 | 8.61 | 291.28 | 2.28 | 1.95 | 249.34 | 0.15 | 19.5 | 0.13 | 0.76 | 0.34 | 0.20 | 0.20 | 19.50 |
| 1000 | 11.49 | 388.38 | 3.03 | 2.60 | 332.45 | 0.20 | 26 | 0.18 | 1.01 | 0.46 | 0.27 | 0.27 | 26.00 |
| 1250 | 14.36 | 485.47 | 3.79 | 3.25 | 415.56 | 0.25 | 32.5 | 0.22 | 1.26 | 0.57 | 0.33 | 0.33 | 32.50 |

TABLE 3-continued

|  | Total Volume | | | H$_2$O | | MDS | | WA | Urea | | MT | GN | Iron |
|---|---|---|---|---|---|---|---|---|---|---|---|---|---|
| SQ | L | oz | gal | gal | oz | gal | oz | oz | lbs | kg | oz | oz | oz |
| 1500 | 17.23 | 582.57 | 4.55 | 3.90 | 498.67 | 0.30 | 39 | 0.26 | 1.51 | 0.69 | 0.40 | 0.40 | 39.00 |
| 1750 | 20.14 | 680.86 | 5.32 | 4.55 | 582.99 | 0.36 | 45.5 | 0.31 | 1.76 | 0.80 | 0.46 | 0.46 | 45.50 |
| 2000 | 23.01 | 777.95 | 6.08 | 5.20 | 666.10 | 0.41 | 52 | 0.35 | 2.01 | 0.91 | 0.53 | 0.53 | 52.00 |
| 2250 | 25.88 | 875.05 | 6.84 | 5.85 | 749.21 | 0.46 | 58.5 | 0.40 | 2.27 | 1.03 | 0.60 | 0.60 | 58.50 |
| 2500 | 28.75 | 972.14 | 7.59 | 6.50 | 832.32 | 0.51 | 65 | 0.44 | 2.52 | 1.14 | 0.66 | 0.66 | 65.00 |
| 2750 | 31.62 | 1069.24 | 8.35 | 7.15 | 915.44 | 0.56 | 71.5 | 0.48 | 2.77 | 1.26 | 0.73 | 0.73 | 71.50 |
| 3000 | 34.49 | 1166.33 | 9.11 | 7.80 | 998.55 | 0.61 | 78 | 0.53 | 3.02 | 1.37 | 0.80 | 0.80 | 78.00 |
| 3250 | 37.36 | 1263.43 | 9.87 | 8.45 | 1081.66 | 0.66 | 84.5 | 0.57 | 3.27 | 1.48 | 0.86 | 0.86 | 84.50 |
| 3500 | 40.24 | 1360.52 | 10.63 | 9.10 | 1164.77 | 0.71 | 91 | 0.61 | 3.52 | 1.60 | 0.93 | 0.93 | 91.00 |
| 3750 | 43.11 | 1457.61 | 11.39 | 9.75 | 1247.89 | 0.76 | 97.5 | 0.66 | 3.78 | 1.71 | 0.99 | 0.99 | 97.50 |
| 4000 | 45.98 | 1554.71 | 12.15 | 10.40 | 1331.00 | 0.81 | 104 | 0.70 | 4.03 | 1.83 | 1.06 | 1.06 | 104.00 |
| 4250 | 48.85 | 1651.80 | 12.90 | 11.05 | 1414.11 | 0.86 | 110.5 | 0.75 | 4.28 | 1.94 | 1.13 | 1.13 | 110.50 |
| 4500 | 51.72 | 1748.90 | 13.66 | 11.70 | 1497.22 | 0.91 | 117 | 0.79 | 4.53 | 2.06 | 1.19 | 1.19 | 117.00 |
| 4750 | 54.63 | 1847.19 | 14.43 | 12.36 | 1581.53 | 0.96 | 123.5 | 0.83 | 4.78 | 2.17 | 1.26 | 1.26 | 123.50 |
| 5000 | 57.50 | 1944.29 | 15.19 | 13.01 | 1664.65 | 1.02 | 130 | 0.88 | 5.03 | 2.28 | 1.33 | 1.33 | 130.00 |
| 5250 | 60.37 | 2041.38 | 15.95 | 13.65 | 1747.76 | 1.07 | 136.5 | 0.92 | 5.29 | 2.40 | 1.39 | 1.39 | 136.50 |
| 5500 | 63.24 | 2138.47 | 16.71 | 14.30 | 1830.87 | 1.12 | 143 | 0.97 | 5.54 | 2.51 | 1.46 | 1.46 | 143.00 |
| 5750 | 66.11 | 2235.57 | 17.47 | 14.95 | 1913.98 | 1.17 | 149.5 | 1.01 | 5.79 | 2.63 | 1.52 | 1.52 | 149.50 |
| 6000 | 68.99 | 2332.66 | 18.22 | 15.60 | 1997.10 | 1.22 | 156 | 1.05 | 6.04 | 2.74 | 1.59 | 1.59 | 156.00 |
| 6250 | 71.86 | 2429.76 | 18.98 | 16.25 | 2080.21 | 1.27 | 162.5 | 1.10 | 6.29 | 2.85 | 1.66 | 1.66 | 162.50 |
| 6500 | 74.73 | 2526.85 | 19.74 | 16.90 | 2163.32 | 1.32 | 169 | 1.14 | 6.54 | 2.97 | 1.72 | 1.72 | 169.00 |
| 6750 | 77.60 | 2623.95 | 20.50 | 17.55 | 2246.43 | 1.37 | 175.5 | 1.19 | 6.80 | 3.08 | 1.79 | 1.79 | 175.50 |
| 7000 | 80.47 | 2721.04 | 21.26 | 18.20 | 2329.55 | 1.42 | 182 | 1.23 | 7.05 | 3.20 | 1.86 | 1.86 | 182.00 |
| 7250 | 83.34 | 2818.13 | 22.02 | 18.85 | 2412.66 | 1.47 | 188.5 | 1.27 | 7.30 | 3.31 | 1.92 | 1.92 | 188.50 |
| 7500 | 86.21 | 2915.23 | 22.78 | 19.50 | 2495.77 | 1.52 | 195 | 1.32 | 7.55 | 3.43 | 1.99 | 1.99 | 195.00 |
| 7750 | 89.12 | 3013.52 | 23.54 | 20.16 | 2580.08 | 1.57 | 201.5 | 1.36 | 7.80 | 3.54 | 2.05 | 2.05 | 201.50 |
| 8000 | 91.99 | 3110.62 | 24.30 | 20.81 | 2663.20 | 1.63 | 208 | 1.40 | 8.05 | 3.65 | 2.12 | 2.12 | 208.00 |
| 8250 | 94.86 | 3207.71 | 25.06 | 21.46 | 2746.31 | 1.68 | 214.5 | 1.45 | 8.31 | 3.77 | 2.19 | 2.19 | 214.50 |
| 8500 | 97.73 | 3304.81 | 25.82 | 22.10 | 2829.42 | 1.73 | 221 | 1.49 | 8.56 | 3.88 | 2.25 | 2.25 | 221.00 |
| 8750 | 100.61 | 3401.90 | 26.58 | 22.75 | 2912.53 | 1.78 | 227.5 | 1.54 | 8.81 | 4.00 | 2.32 | 2.32 | 227.50 |
| 9000 | 103.48 | 3498.99 | 27.34 | 23.40 | 2995.65 | 1.83 | 234 | 1.58 | 9.06 | 4.11 | 2.39 | 2.39 | 234.00 |

As shown in Table 3 above, the composition of Example 2 comprises approximately 6.69% iron HEDTA (ounces of iron/total ounces), 0.07% micromate (ounces of micromate/total ounces), 0.07% glycerin (ounces of glycerin/total ounces), 3.97% to 3.98% Urea (kilograms Urea/total liters), 0.05% natural-based wetting agent (ounces of wetting agent/total ounces), and 6.69% MDS (gallons of MDS/total gallons).

Table 4 below shows the percent measurements of the ingredients provided in Table 3. The square footage is shown in column one. The total volume is shown in three units of measurement: Liters (L) (column 2), ounces (oz) (column 3) and gallons (gal) (column 4). Columns 5 and 6 show the amount of water in gallons and ounces. In column 7, the percent iron HEDTA is shown by volume, in column 8 the percent micromate is shown by volume, in column 9 the percent feed grade urea is shown by weight to volume, column 10 shows the percent natural-based wetting agent (WA) by volume, and column 11 shows the amount of MDS by volume.

TABLE 4

|  | Total Volume | | | H$_2$O | | Iron | Micromate | Urea | WA | MDS |
|---|---|---|---|---|---|---|---|---|---|---|
| SQ | L | oz | gal | gal | oz | (oz/oz) % | (oz/oz) % | (kg/L) % | (oz/oz) % | (gal/gal) % |
| 250 | 2.87 | 97.09 | 0.76 | 0.65 | 83.11 | 6.6945 | 0.0682 | 3.9762 | 0.0452 | 6.69 |
| 500 | 5.74 | 194.19 | 1.52 | 1.30 | 166.22 | 6.6945 | 0.0682 | 3.9762 | 0.0452 | 6.69 |
| 750 | 8.61 | 291.28 | 2.28 | 1.95 | 249.34 | 6.6945 | 0.0682 | 3.9762 | 0.0452 | 6.69 |
| 1000 | 11.49 | 388.38 | 3.03 | 2.60 | 332.45 | 6.6945 | 0.0682 | 3.9762 | 0.0452 | 6.69 |
| 1250 | 14.36 | 485.47 | 3.79 | 3.25 | 415.56 | 6.6945 | 0.0682 | 3.9762 | 0.0452 | 6.69 |
| 1500 | 17.23 | 582.57 | 4.55 | 3.90 | 498.67 | 6.6945 | 0.0682 | 3.9762 | 0.0452 | 6.69 |
| 1750 | 20.14 | 680.86 | 5.32 | 4.55 | 582.99 | 6.6827 | 0.0681 | 3.9692 | 0.0451 | 6.68 |
| 2000 | 23.01 | 777.95 | 6.08 | 5.20 | 666.10 | 6.6842 | 0.0681 | 3.9700 | 0.0451 | 6.68 |
| 2250 | 25.88 | 875.05 | 6.84 | 5.85 | 749.21 | 6.6853 | 0.0682 | 3.9707 | 0.0452 | 6.69 |
| 2500 | 28.75 | 972.14 | 7.59 | 6.50 | 832.32 | 6.6863 | 0.0682 | 3.9713 | 0.0452 | 6.69 |
| 2750 | 31.62 | 1069.24 | 8.35 | 7.15 | 915.44 | 6.6870 | 0.0682 | 3.9717 | 0.0452 | 6.69 |
| 3000 | 34.49 | 1166.33 | 9.11 | 7.80 | 998.55 | 6.6876 | 0.0682 | 3.9721 | 0.0452 | 6.69 |
| 3250 | 37.36 | 1263.43 | 9.87 | 8.45 | 1081.66 | 6.6882 | 0.0682 | 3.9724 | 0.0452 | 6.69 |
| 3500 | 40.24 | 1360.52 | 10.63 | 9.10 | 1164.77 | 6.6886 | 0.0682 | 3.9727 | 0.0452 | 6.69 |
| 3750 | 43.11 | 1457.61 | 11.39 | 9.75 | 1247.89 | 6.6890 | 0.0682 | 3.9729 | 0.0452 | 6.69 |
| 4000 | 45.98 | 1554.71 | 12.15 | 10.40 | 1331.00 | 6.6894 | 0.0682 | 3.9731 | 0.0452 | 6.69 |
| 4250 | 48.85 | 1651.80 | 12.90 | 11.05 | 1414.11 | 6.6897 | 0.0682 | 3.9733 | 0.0452 | 6.69 |
| 4500 | 51.72 | 1748.90 | 13.66 | 11.70 | 1497.22 | 6.6899 | 0.0682 | 3.9734 | 0.0452 | 6.69 |
| 4750 | 54.63 | 1847.19 | 14.43 | 12.36 | 1581.53 | 6.6858 | 0.0682 | 3.9710 | 0.0452 | 6.69 |
| 5000 | 57.50 | 1944.29 | 15.19 | 13.01 | 1664.65 | 6.6863 | 0.0682 | 3.9713 | 0.0452 | 6.69 |
| 5250 | 60.37 | 2041.38 | 15.95 | 13.65 | 1747.76 | 6.6867 | 0.0682 | 3.9715 | 0.0452 | 6.69 |
| 5500 | 63.24 | 2138.47 | 16.71 | 14.30 | 1830.87 | 6.6870 | 0.0682 | 3.9717 | 0.0452 | 6.69 |

TABLE 4-continued

| | Total Volume | | H₂O | | Iron | Micromate | Urea | WA | MDS |
|---|---|---|---|---|---|---|---|---|---|
| SQ | L | oz | gal | oz | (oz/oz) % | (oz/oz) % | (kg/L) % | (oz/oz) % | (gal/gal) % |
| 5750 | 66.11 | 2235.57 | 17.47 | 14.95 1913.98 | 6.6873 | 0.0682 | 3.9719 | 0.0452 | 6.69 |
| 6000 | 68.99 | 2332.66 | 18.22 | 15.60 1997.10 | 6.6876 | 0.0682 | 3.9721 | 0.0452 | 6.69 |
| 6250 | 71.86 | 2429.76 | 18.98 | 16.25 2080.21 | 6.6879 | 0.0682 | 3.9722 | 0.0452 | 6.69 |
| 6500 | 74.73 | 2526.85 | 19.74 | 16.90 2163.32 | 6.6882 | 0.0682 | 3.9724 | 0.0452 | 6.69 |
| 6750 | 77.60 | 2623.95 | 20.50 | 17.55 2246.43 | 6.6884 | 0.0682 | 3.9725 | 0.0452 | 6.69 |
| 7000 | 80.47 | 2721.04 | 21.26 | 18.20 2329.55 | 6.6886 | 0.0682 | 3.9727 | 0.0452 | 6.69 |
| 7250 | 83.34 | 2818.13 | 22.02 | 18.85 2412.66 | 6.6888 | 0.0682 | 3.9728 | 0.0452 | 6.69 |
| 7500 | 86.21 | 2915.23 | 22.78 | 19.50 2495.77 | 6.6890 | 0.0682 | 3.9729 | 0.0452 | 6.69 |
| 7750 | 89.12 | 3013.52 | 23.54 | 20.16 2580.08 | 6.6865 | 0.0682 | 3.9714 | 0.0452 | 6.69 |
| 8000 | 91.99 | 3110.62 | 24.30 | 20.81 2663.20 | 6.6868 | 0.0682 | 3.9716 | 0.0452 | 6.69 |
| 8250 | 94.86 | 3207.71 | 25.06 | 21.46 2746.31 | 6.6870 | 0.0682 | 3.9717 | 0.0452 | 6.69 |
| 8500 | 97.73 | 3304.81 | 25.82 | 22.10 2829.42 | 6.6872 | 0.0682 | 3.9718 | 0.0452 | 6.69 |
| 8750 | 100.61 | 3401.90 | 26.58 | 22.75 2912.53 | 6.6874 | 0.0682 | 3.9720 | 0.0452 | 6.69 |
| 9000 | 103.48 | 3498.99 | 27.34 | 23.40 2995.65 | 6.6876 | 0.0682 | 3.9721 | 0.0452 | 6.69 |

As shown in Table 4 above, the composition of Example 2 comprises approximately 6.69% iron HEDTA (ounces of iron/total ounces), 0.07% micromate (ounces of micromate/total ounces), 3.98% Urea (kilograms Urea/total liters), 0.05% natural-based wetting agent (ounces of wetting agent/total ounces), and 6.69% MDS (gallons of MDS/total gallons). The composition may further comprise 0.07% glycerin (ounces of glycerin/total ounces) (not shown in Table 4).

For example, row 3 shows the amount of each ingredient used as well as the total volume used to treat 10,000 square feet. The total volume/square foot equates to between 0.3 ounces and 0.4 ounces per square foot. The final composition may be applied by any of the methods described above directly to the soil, lawn, or a cultivated area, for example.

Example 3

In Table 5 below different measurements of the ingredients are provided to treat from 10,000 square feet to 100,000 square feet (SQ), column one. The total volume is shown in two units of measurement: Liters (L) (column 2), and gallons (column 3). Columns 4 to 7 show the amount of water and MDS in two units of measurement, gallons and ounces. In column 8, the amount of natural-based wetting agent (WA) is shown in ounces. In columns 9 and 10, the amount of feed grade urea is shown in pounds (lbs) and kilograms (kg), respectively. In column 11, the amount of micromate (MT) is shown in ounces. In column 12, the amount of glycerin (GN) is shown in ounces. Lastly, in column 13, the amount of iron HEDTA is shown in ounces.

TABLE 5

| | Total Volume | | H2O | | MDS | | WA | Urea | | MT | GN | Iron |
|---|---|---|---|---|---|---|---|---|---|---|---|---|
| SQ | L | gal | gal | oz | gal | oz | oz | lbs | kg | oz | oz | oz |
| 10000 | 115 | 30 | 26 | 3328 | 2.03 | 260 | 1.76 | 10.07 | 4.57 | 2.65 | 2.65 | 260 |
| 15000 | 172 | 46 | 39 | 4993 | 3.05 | 390 | 2.63 | 15.10 | 6.85 | 3.98 | 3.98 | 390 |
| 20000 | 230 | 61 | 52 | 6657 | 4.06 | 520 | 3.51 | 20.14 | 9.13 | 5.30 | 5.30 | 520 |
| 25000 | 287 | 76 | 65 | 8321 | 5.08 | 650 | 4.39 | 25.17 | 11.42 | 6.63 | 6.63 | 650 |
| 30000 | 345 | 91 | 78 | 9985 | 6.09 | 780 | 5.27 | 30.20 | 13.70 | 7.95 | 7.95 | 780 |
| 35000 | 402 | 106 | 91 | 11650 | 7.11 | 910 | 6.15 | 35.24 | 15.98 | 9.28 | 9.28 | 910 |
| 40000 | 460 | 121 | 104 | 13314 | 8.13 | 1040 | 7.02 | 40.27 | 18.27 | 10.60 | 10.60 | 1040 |
| 45000 | 517 | 137 | 117 | 14978 | 9.14 | 1170 | 7.90 | 45.31 | 20.55 | 11.93 | 11.93 | 1170 |
| 50000 | 575 | 152 | 130 | 16643 | 10.16 | 1300 | 8.78 | 50.34 | 22.83 | 13.25 | 13.25 | 1300 |
| 55000 | 632 | 167 | 143 | 18306 | 11.17 | 1430 | 9.66 | 55.38 | 25.12 | 14.58 | 14.58 | 1430 |
| 60000 | 690 | 182 | 156 | 19971 | 12.19 | 1560 | 10.54 | 60.41 | 27.40 | 15.90 | 15.90 | 1560 |
| 65000 | 747 | 197 | 169 | 21636 | 13.20 | 1690 | 11.41 | 65.44 | 29.68 | 17.23 | 17.23 | 1690 |
| 70000 | 805 | 213 | 182 | 23299 | 14.22 | 1820 | 12.29 | 70.48 | 31.97 | 18.55 | 18.55 | 1820 |
| 75000 | 862 | 228 | 195 | 24964 | 15.23 | 1950 | 13.17 | 75.51 | 34.25 | 19.88 | 19.88 | 1950 |
| 80000 | 920 | 243 | 208 | 26628 | 16.25 | 2080 | 14.05 | 80.55 | 36.54 | 21.20 | 21.20 | 2080 |
| 85000 | 977 | 258 | 221 | 28292 | 17.27 | 2210 | 14.93 | 85.58 | 38.82 | 22.53 | 22.53 | 2210 |
| 90000 | 1035 | 273 | 234 | 29956 | 18.28 | 2340 | 15.80 | 90.61 | 41.10 | 23.85 | 23.85 | 2340 |
| 95000 | 1092 | 289 | 247 | 31621 | 19.30 | 2470 | 16.68 | 95.65 | 43.39 | 25.18 | 25.18 | 2470 |
| 100000 | 1150 | 304 | 260 | 33285 | 20.31 | 2600 | 17.56 | 100.68 | 45.67 | 26.51 | 26.51 | 2600 |

Table 6 below shows the percent measurements of the ingredients provided in Table 5. The square footage is shown in column one. In column 2 the percent iron HEDTA is shown by volume, in column 3 the percent micromate is shown by volume, in column 4 the percent feed grade urea is shown by weight to volume, column 5 shows the percent natural-based wetting agent (WA) by volume, and column 6 shows the amount of MDS by volume.

TABLE 6

| SQ | Iron (oz/oz) % | Micromate (oz/oz) % | Urea (kg/L) % | WA (oz/oz) % | MDS (gal/gal) % |
|---|---|---|---|---|---|
| 10000 | 6.6883 | 0.0682 | 3.9725 | 0.0452 | 6.69 |
| 15000 | 6.6876 | 0.0682 | 3.9721 | 0.0452 | 6.69 |
| 20000 | 6.6873 | 0.0682 | 3.9719 | 0.0452 | 6.69 |
| 25000 | 6.6879 | 0.0682 | 3.9722 | 0.0452 | 6.69 |
| 30000 | 6.6876 | 0.0682 | 3.9721 | 0.0452 | 6.69 |

TABLE 6-continued

| SQ | Iron (oz/oz) % | Micromate (oz/oz) % | Urea (kg/L) % | WA (oz/oz) % | MDS (gal/gal) % |
|---|---|---|---|---|---|
| 35000 | 6.6874 | 0.0682 | 3.9720 | 0.0452 | 6.69 |
| 40000 | 6.6878 | 0.0682 | 3.9722 | 0.0452 | 6.69 |
| 45000 | 6.6876 | 0.0682 | 3.9721 | 0.0452 | 6.69 |
| 50000 | 6.6875 | 0.0682 | 3.9720 | 0.0452 | 6.69 |
| 55000 | 6.6878 | 0.0682 | 3.9722 | 0.0452 | 6.69 |
| 60000 | 6.6876 | 0.0682 | 3.9721 | 0.0452 | 6.69 |
| 65000 | 6.6875 | 0.0682 | 3.9720 | 0.0452 | 6.69 |
| 70000 | 6.6877 | 0.0682 | 3.9721 | 0.0452 | 6.69 |
| 75000 | 6.6876 | 0.0682 | 3.9721 | 0.0452 | 6.69 |
| 80000 | 6.6876 | 0.0682 | 3.9720 | 0.0452 | 6.69 |
| 85000 | 6.6877 | 0.0682 | 3.9721 | 0.0452 | 6.69 |
| 90000 | 6.6876 | 0.0682 | 3.9721 | 0.0452 | 6.69 |
| 95000 | 6.6876 | 0.0682 | 3.9720 | 0.0452 | 6.69 |
| 100000 | 6.6877 | 0.0682 | 3.9721 | 0.0452 | 6.69 |

As shown in Table 6 above, the composition of Example 3 comprises approximately 6.69% iron HEDTA (ounces of iron/total ounces), 0.07% micromate (ounces of micromate/total ounces), 3.98% Urea (kilograms Urea/total liters), 0.05% natural-based wetting agent (ounces of wetting agent/total ounces), and 6.69% MDS (gallons of MDS/total gallons). The composition may further comprise 0.07% glycerin (ounces of glycerin/total ounces) (not shown in Table 6).

Example 4

In Table 7 below different measurements of the ingredients are provided to treat from 250 square feet to 9,000 square feet (SQ), column one. The total volume is shown in three units of measurement: Liters (L) (column 2), ounces (oz) (column 3) and gallons (gal) (column 4). Columns 5 through 8 show the amount of water and MDS in two units of measurement, gallons and ounces. In column 9, the amount of natural-based wetting agent (WA) is shown in ounces. In columns 10 and 11, the amount of feed grade urea is shown in pounds (lbs) and kilograms (kg), respectively. In column 12, the amount of micromate (MT) is shown in ounces. In column 13, the amount of glycerin (GN) is shown in ounces. Lastly, in column 14, the amount of iron HEDTA is shown in ounces.

For example, row 3 shows the amount of each ingredient used as well as the total volume used to treat 250 square feet. The total volume/square foot equates to between 0.3 ounces and 0.4 ounces per square foot. The final composition may be applied by any of the methods described above directly to the soil, lawn, or a cultivated area, for example.

TABLE 7

| SQ | Total Volume | | | H₂O | | MDS | | WA | Urea | | MT | GN | Iron |
|---|---|---|---|---|---|---|---|---|---|---|---|---|---|
| | L | oz | gal | gal | oz | gal | oz | oz | lbs | kg | oz | oz | oz |
| 250 | 2.84 | 96.00 | 0.75 | 0.63 | 80.6 | 0.07 | 9.0 | 0.04 | 0.25 | 0.11 | 0.07 | 0.07 | 6.5 |
| 500 | 5.68 | 192.00 | 1.50 | 1.25 | 160.0 | 0.15 | 19.2 | 0.09 | 0.50 | 0.23 | 0.13 | 0.13 | 13.0 |
| 750 | 8.56 | 289.28 | 2.26 | 1.88 | 240.6 | 0.22 | 28.2 | 0.13 | 0.76 | 0.34 | 0.20 | 0.20 | 19.5 |
| 1000 | 11.39 | 385.28 | 3.01 | 2.50 | 320.0 | 0.30 | 38.4 | 0.18 | 1.01 | 0.46 | 0.27 | 0.27 | 26.0 |
| 1250 | 14.23 | 481.28 | 3.76 | 3.13 | 400.6 | 0.37 | 47.4 | 0.22 | 1.26 | 0.57 | 0.33 | 0.33 | 32.5 |
| 1500 | 17.07 | 577.28 | 4.51 | 3.75 | 480.0 | 0.45 | 57.6 | 0.26 | 1.51 | 0.69 | 0.40 | 0.40 | 39.0 |
| 1750 | 19.95 | 674.56 | 5.27 | 4.38 | 560.6 | 0.53 | 67.8 | 0.31 | 1.76 | 0.80 | 0.46 | 0.46 | 45.5 |
| 2000 | 22.79 | 770.56 | 6.02 | 5.00 | 640.0 | 0.61 | 78.1 | 0.35 | 2.01 | 0.91 | 0.53 | 0.53 | 52.0 |
| 2250 | 25.67 | 867.84 | 6.78 | 5.63 | 720.6 | 0.68 | 87.0 | 0.40 | 2.27 | 1.03 | 0.60 | 0.60 | 58.5 |
| 2500 | 28.50 | 963.84 | 7.53 | 6.25 | 800.0 | 0.76 | 97.3 | 0.44 | 2.52 | 1.14 | 0.66 | 0.66 | 65.0 |
| 2750 | 31.34 | 1059.84 | 8.28 | 6.88 | 880.6 | 0.83 | 106.2 | 0.48 | 2.77 | 1.26 | 0.73 | 0.73 | 71.5 |
| 3000 | 34.18 | 1155.84 | 9.03 | 7.50 | 960.0 | 0.91 | 116.5 | 0.53 | 3.02 | 1.37 | 0.80 | 0.80 | 78.0 |
| 3250 | 37.02 | 1251.84 | 9.78 | 8.13 | 1040.6 | 0.98 | 125.4 | 0.57 | 3.27 | 1.48 | 0.86 | 0.86 | 84.5 |
| 3500 | 39.86 | 1347.84 | 10.53 | 8.75 | 1120.0 | 1.06 | 135.7 | 0.61 | 3.52 | 1.60 | 0.93 | 0.93 | 91.0 |
| 3750 | 42.74 | 1445.12 | 11.29 | 9.38 | 1200.6 | 1.13 | 144.6 | 0.66 | 3.78 | 1.71 | 0.99 | 0.99 | 97.5 |
| 4000 | 45.58 | 1541.12 | 12.04 | 10.00 | 1280.0 | 1.21 | 154.9 | 0.70 | 4.03 | 1.83 | 1.06 | 1.06 | 104.0 |
| 4250 | 48.42 | 1637.12 | 12.79 | 10.63 | 1360.6 | 1.28 | 163.8 | 0.75 | 4.28 | 1.94 | 1.13 | 1.13 | 110.5 |
| 4500 | 51.25 | 1733.12 | 13.54 | 11.25 | 1440.0 | 1.36 | 174.1 | 0.79 | 4.53 | 2.06 | 1.19 | 1.19 | 117.0 |
| 4750 | 54.13 | 1830.40 | 14.30 | 11.88 | 1520.6 | 1.44 | 184.3 | 0.83 | 4.78 | 2.17 | 1.26 | 1.26 | 123.5 |
| 5000 | 56.97 | 1926.40 | 15.05 | 12.50 | 1600.0 | 1.52 | 194.6 | 0.88 | 5.03 | 2.28 | 1.33 | 1.33 | 130.0 |
| 5250 | 59.85 | 2023.68 | 15.81 | 13.13 | 1680.6 | 1.59 | 203.5 | 0.92 | 5.29 | 2.40 | 1.39 | 1.39 | 136.5 |
| 5500 | 62.69 | 2119.68 | 16.56 | 13.75 | 1760.0 | 1.67 | 213.8 | 0.97 | 5.54 | 2.51 | 1.46 | 1.46 | 143.0 |
| 5750 | 65.53 | 2215.68 | 17.31 | 14.38 | 1840.6 | 1.74 | 222.7 | 1.01 | 5.79 | 2.63 | 1.52 | 1.52 | 149.5 |
| 6000 | 68.36 | 2311.68 | 18.06 | 15.00 | 1920.0 | 1.82 | 233.0 | 1.05 | 6.04 | 2.74 | 1.59 | 1.59 | 156.0 |
| 6250 | 71.20 | 2407.68 | 18.81 | 15.63 | 2000.6 | 1.89 | 241.9 | 1.10 | 6.29 | 2.85 | 1.66 | 1.66 | 162.5 |
| 6500 | 74.04 | 2503.68 | 19.56 | 16.25 | 2080.0 | 1.97 | 252.2 | 1.14 | 6.54 | 2.97 | 1.72 | 1.72 | 169.0 |
| 6750 | 76.92 | 2600.96 | 20.32 | 16.88 | 2160.6 | 2.04 | 261.1 | 1.19 | 6.80 | 3.08 | 1.79 | 1.79 | 175.5 |
| 7000 | 79.76 | 2696.96 | 21.07 | 17.50 | 2240.0 | 2.12 | 271.4 | 1.23 | 7.05 | 3.20 | 1.86 | 1.86 | 182.0 |
| 7250 | 82.60 | 2792.96 | 21.82 | 18.13 | 2320.6 | 2.19 | 280.3 | 1.27 | 7.30 | 3.31 | 1.92 | 1.92 | 188.5 |
| 7500 | 85.44 | 2888.96 | 22.57 | 18.76 | 2401.3 | 2.27 | 290.6 | 1.32 | 7.55 | 3.43 | 1.99 | 1.99 | 195.0 |
| 7750 | 88.31 | 2986.24 | 23.33 | 19.38 | 2480.6 | 2.35 | 300.8 | 1.36 | 7.80 | 3.54 | 2.05 | 2.05 | 201.5 |
| 8000 | 91.15 | 3082.24 | 24.08 | 20.01 | 2561.3 | 2.43 | 311.0 | 1.40 | 8.05 | 3.65 | 2.12 | 2.12 | 208.0 |
| 8250 | 94.03 | 3179.52 | 24.84 | 20.63 | 2640.6 | 2.50 | 320.0 | 1.45 | 8.31 | 3.77 | 2.19 | 2.19 | 214.5 |
| 8500 | 96.87 | 3275.52 | 25.59 | 21.26 | 2721.3 | 2.58 | 330.2 | 1.49 | 8.56 | 3.88 | 2.25 | 2.25 | 221.0 |
| 8750 | 99.71 | 3371.52 | 26.34 | 21.88 | 2800.6 | 2.65 | 339.2 | 1.54 | 8.81 | 4.00 | 2.32 | 2.32 | 227.5 |
| 9000 | 102.55 | 3467.52 | 27.09 | 22.51 | 2881.3 | 2.73 | 349.4 | 1.58 | 9.06 | 4.11 | 2.39 | 2.39 | 234.0 |

Table 8 below shows the percent measurements of the ingredients provided in Table 7. The square footage is shown in column one. The total volume is shown in three units of measurement: Liters (L) (column 2), ounces (oz) (column 3) and gallons (gal) (column 4). Columns 5 and 6 show the amount of water in gallons and ounces. In column 7, the percent iron HEDTA is shown by volume, in column 8 the percent micromate is shown by volume, in column 9 the percent feed grade urea is shown by weight to volume, column 10 shows the percent natural-based wetting agent (WA) by volume, and column 11 shows the amount of MDS by volume.

Example 5

In Table 9 below different measurements of the ingredients are provided to treat from 10,000 square feet to 100,000 square feet (SQ), column one. The total volume is shown in two units of measurement: Liters (L) (column 2), and gallons (column 3). Columns 4 to 7 show the amount of water and MDS in two units of measurement, gallons and ounces. In column 8, the amount of natural-based wetting agent (WA) is shown in ounces. In columns 9 and 10, the amount of feed grade urea is shown in pounds (lbs) and kilograms (kg), respectively. In column 11, the amount of

TABLE 8

| | Total Volume | | | H₂O | | Iron | Micromate | Urea | WA | MDS |
|---|---|---|---|---|---|---|---|---|---|---|
| SQ | L | oz | gal | gal | oz | (oz/oz) % | (oz/oz) % | (kg/L) % | (oz/oz) % | (gal/gal) % |
| 250 | 2.84 | 96.00 | 0.75 | 0.63 | 80.6 | 6.7708 | 0.0690 | 4.0215 | 0.0457 | 9.3333 |
| 500 | 5.68 | 192.00 | 1.50 | 1.25 | 160.0 | 6.7708 | 0.0690 | 4.0215 | 0.0457 | 10.0000 |
| 750 | 8.56 | 289.28 | 2.26 | 1.88 | 240.6 | 6.7409 | 0.0687 | 4.0037 | 0.0455 | 9.7345 |
| 1000 | 11.39 | 385.28 | 3.01 | 2.50 | 320.0 | 6.7483 | 0.0688 | 4.0081 | 0.0456 | 9.9668 |
| 1250 | 14.23 | 481.28 | 3.76 | 3.13 | 400.6 | 6.7528 | 0.0688 | 4.0108 | 0.0456 | 9.8404 |
| 1500 | 17.07 | 577.28 | 4.51 | 3.75 | 480.0 | 6.7558 | 0.0689 | 4.0126 | 0.0456 | 9.9778 |
| 1750 | 19.95 | 674.56 | 5.27 | 4.38 | 560.6 | 6.7451 | 0.0688 | 4.0062 | 0.0456 | 10.0569 |
| 2000 | 22.79 | 770.56 | 6.02 | 5.00 | 640.0 | 6.7483 | 0.0688 | 4.0081 | 0.0456 | 10.1329 |
| 2250 | 25.67 | 867.84 | 6.78 | 5.63 | 720.6 | 6.7409 | 0.0687 | 4.0037 | 0.0455 | 10.0295 |
| 2500 | 28.50 | 963.84 | 7.53 | 6.25 | 800.0 | 6.7439 | 0.0687 | 4.0055 | 0.0455 | 10.0930 |
| 2750 | 31.34 | 1059.84 | 8.28 | 6.88 | 880.6 | 6.7463 | 0.0688 | 4.0069 | 0.0456 | 10.0242 |
| 3000 | 34.18 | 1155.84 | 9.03 | 7.50 | 960.0 | 6.7483 | 0.0688 | 4.0081 | 0.0456 | 10.0775 |
| 3250 | 37.02 | 1251.84 | 9.78 | 8.13 | 1040.6 | 6.7501 | 0.0688 | 4.0092 | 0.0456 | 10.0204 |
| 3500 | 39.86 | 1347.84 | 10.53 | 8.75 | 1120.0 | 6.7515 | 0.0688 | 4.0100 | 0.0456 | 10.0665 |
| 3750 | 42.74 | 1445.12 | 11.29 | 9.38 | 1200.6 | 6.7468 | 0.0688 | 4.0072 | 0.0456 | 10.0089 |
| 4000 | 45.58 | 1541.12 | 12.04 | 10.00 | 1280.0 | 6.7483 | 0.0688 | 4.0081 | 0.0456 | 10.0498 |
| 4250 | 48.42 | 1637.12 | 12.79 | 10.63 | 1360.6 | 6.7497 | 0.0688 | 4.0089 | 0.0456 | 10.0078 |
| 4500 | 51.25 | 1733.12 | 13.54 | 11.25 | 1440.0 | 6.7508 | 0.0688 | 4.0096 | 0.0456 | 10.0443 |
| 4750 | 54.13 | 1830.40 | 14.30 | 11.88 | 1520.6 | 6.7472 | 0.0688 | 4.0074 | 0.0456 | 10.0699 |
| 5000 | 56.97 | 1926.40 | 15.05 | 12.50 | 1600.0 | 6.7483 | 0.0688 | 4.0081 | 0.0456 | 10.0997 |
| 5250 | 59.85 | 2023.68 | 15.81 | 13.13 | 1680.6 | 6.7451 | 0.0688 | 4.0062 | 0.0456 | 10.0569 |
| 5500 | 62.69 | 2119.68 | 16.56 | 13.75 | 1760.0 | 6.7463 | 0.0688 | 4.0069 | 0.0456 | 10.0845 |
| 5750 | 65.53 | 2215.68 | 17.31 | 14.38 | 1840.6 | 6.7474 | 0.0688 | 4.0076 | 0.0456 | 10.0520 |
| 6000 | 68.36 | 2311.68 | 18.06 | 15.00 | 1920.0 | 6.7483 | 0.0688 | 4.0081 | 0.0456 | 10.0775 |
| 6250 | 71.20 | 2407.68 | 18.81 | 15.63 | 2000.6 | 6.7492 | 0.0688 | 4.0087 | 0.0456 | 10.0478 |
| 6500 | 74.04 | 2503.68 | 19.56 | 16.25 | 2080.0 | 6.7501 | 0.0688 | 4.0092 | 0.0456 | 10.0716 |
| 6750 | 76.92 | 2600.96 | 20.32 | 16.88 | 2160.6 | 6.7475 | 0.0688 | 4.0076 | 0.0456 | 10.0394 |
| 7000 | 79.76 | 2696.96 | 21.07 | 17.50 | 2240.0 | 6.7483 | 0.0688 | 4.0081 | 0.0456 | 10.0617 |
| 7250 | 82.60 | 2792.96 | 21.82 | 18.13 | 2320.6 | 6.7491 | 0.0688 | 4.0086 | 0.0456 | 10.0367 |
| 7500 | 85.44 | 2888.96 | 22.57 | 18.76 | 2401.3 | 6.7498 | 0.0688 | 4.0090 | 0.0456 | 10.0576 |
| 7750 | 88.31 | 2986.24 | 23.33 | 19.38 | 2480.6 | 6.7476 | 0.0688 | 4.0077 | 0.0456 | 10.0729 |
| 8000 | 91.15 | 3082.24 | 24.08 | 20.01 | 2561.3 | 6.7483 | 0.0688 | 4.0081 | 0.0456 | 10.0914 |
| 8250 | 94.03 | 3179.52 | 24.84 | 20.63 | 2640.6 | 6.7463 | 0.0688 | 4.0069 | 0.0456 | 10.0644 |
| 8500 | 96.87 | 3275.52 | 25.59 | 21.26 | 2721.3 | 6.7470 | 0.0688 | 4.0073 | 0.0456 | 10.0821 |
| 8750 | 99.71 | 3371.52 | 26.34 | 21.88 | 2800.6 | 6.7477 | 0.0688 | 4.0077 | 0.0456 | 10.0607 |
| 9000 | 102.55 | 3467.52 | 27.09 | 22.51 | 2881.3 | 6.7483 | 0.0688 | 4.0081 | 0.0456 | 10.0775 |

As shown in Table 8 above, the composition of Example 4 comprises approximately 6.77% to 6.75% iron HEDTA (ounces of iron/total ounces), 0.07% micromate (ounces of micromate/total ounces), 4.00% to 4.02% Urea (kilograms Urea/total liters), 0.05% natural-based wetting agent (ounces of wetting agent/total ounces), and 9.33% to 10.1% MDS (gallons of MDS/total gallons). The composition may further comprise 0.07% glycerin (ounces of glycerin/total ounces) (not shown in Table 10).

micromate (MT) is shown in ounces. In column 12, the amount of glycerin (GN) is shown in ounces. Lastly, in column 13, the amount of iron HEDTA is shown in ounces.

For example, row 3 shows the amount of each ingredient used as well as the total volume used to treat 10,000 square feet. The total volume/square foot equates to between 0.3 ounces and 0.4 ounces per square foot. The final composition may be applied by any of the methods described above directly to the soil, lawn, or a cultivated area, for example.

TABLE 9

| | Total Volume | | H2O | | MDS | | WA | Urea | | MT | GN | Iron |
|---|---|---|---|---|---|---|---|---|---|---|---|---|
| SQ | L | gal | gal | oz | gal | oz | oz | lbs | kg | oz | oz | oz |
| 10000 | 115 | 30 | 25.01 | 3201 | 3.03 | 387.84 | 1.76 | 10.07 | 4.57 | 2.65 | 2.65 | 260 |
| 15000 | 172 | 46 | 37.51 | 4801 | 4.54 | 581.12 | 2.63 | 15.10 | 6.85 | 3.98 | 3.98 | 390 |
| 20000 | 230 | 61 | 50.01 | 6401 | 6.06 | 775.68 | 3.51 | 20.14 | 9.13 | 5.30 | 5.30 | 520 |
| 25000 | 287 | 76 | 62.52 | 8003 | 7.57 | 968.96 | 4.39 | 25.17 | 11.42 | 6.63 | 6.63 | 650 |
| 30000 | 345 | 91 | 75.02 | 9603 | 9.08 | 1162.24 | 5.27 | 30.20 | 13.70 | 7.95 | 7.95 | 780 |
| 35000 | 402 | 106 | 87.52 | 11203 | 10.60 | 1356.8 | 6.15 | 35.24 | 15.98 | 9.28 | 9.28 | 910 |
| 40000 | 460 | 121 | 100.03 | 12804 | 12.11 | 1550.08 | 7.02 | 40.27 | 18.27 | 10.60 | 10.60 | 1040 |
| 45000 | 517 | 137 | 112.53 | 14404 | 13.63 | 1744.64 | 7.90 | 45.31 | 20.55 | 11.93 | 11.93 | 1170 |
| 50000 | 575 | 152 | 125.03 | 16004 | 15.14 | 1937.92 | 8.78 | 50.34 | 22.83 | 13.25 | 13.25 | 1300 |
| 55000 | 632 | 167 | 137.54 | 17605 | 16.65 | 2131.2 | 9.66 | 55.38 | 25.12 | 14.58 | 14.58 | 1430 |
| 60000 | 690 | 182 | 150.04 | 19205 | 18.17 | 2325.76 | 10.54 | 60.41 | 27.40 | 15.90 | 15.90 | 1560 |
| 65000 | 747 | 197 | 162.54 | 20805 | 19.69 | 2520.32 | 11.41 | 65.44 | 29.68 | 17.23 | 17.23 | 1690 |
| 70000 | 805 | 213 | 175.05 | 22406 | 21.19 | 2712.32 | 12.29 | 70.48 | 31.97 | 18.55 | 18.55 | 1820 |
| 75000 | 862 | 228 | 187.55 | 24006 | 22.71 | 2906.88 | 13.17 | 75.51 | 34.25 | 19.88 | 19.88 | 1950 |
| 80000 | 920 | 243 | 200.05 | 25606 | 24.23 | 3101.44 | 14.05 | 80.55 | 36.54 | 21.20 | 21.20 | 2080 |
| 85000 | 977 | 258 | 212.56 | 27208 | 25.74 | 3294.72 | 14.93 | 85.58 | 38.82 | 22.53 | 22.53 | 2210 |
| 90000 | 1035 | 273 | 225.06 | 28800 | 27.25 | 3488 | 15.80 | 90.61 | 41.10 | 23.85 | 23.85 | 2340 |
| 95000 | 1092 | 289 | 237.56 | 30408 | 28.77 | 3682.56 | 16.68 | 95.65 | 43.39 | 25.18 | 25.18 | 2470 |
| 100000 | 1150 | 304 | 250.07 | 32009 | 30.28 | 3875.84 | 17.56 | 100.68 | 45.67 | 26.51 | 26.51 | 2600 |

Table 10 below shows the percent measurements of the ingredients provided in Table 9. The square footage is shown in column one. The total volume is shown in two units of measurement: Liters (L) (column 2), and gallons (gal) (column 3). In column 4, the percent iron HEDTA is shown by volume, in column 5 the percent micromate is shown by volume, in column 6 the percent feed grade urea is shown by weight to volume, column 7 shows the percent natural-based wetting agent (WA) by volume, and column 8 shows the amount of MDS by volume.

TABLE 10

| | Total Volume | | Iron | Micromate | Urea | WA | MDS |
|---|---|---|---|---|---|---|---|
| SQ | L | gal | (oz/oz) % | (oz/oz) % | (kg/L) % | (oz/oz) % | (gal/gal) % |
| 10000 | 115 | 30 | 6.6866 | 0.0682 | 3.9714 | 0.0452 | 9.97 |
| 15000 | 172 | 46 | 6.6880 | 0.0682 | 3.9723 | 0.0452 | 9.97 |
| 20000 | 230 | 61 | 6.6877 | 0.0682 | 3.9721 | 0.0452 | 9.98 |
| 25000 | 287 | 76 | 6.6874 | 0.0682 | 3.9720 | 0.0452 | 9.97 |
| 30000 | 345 | 91 | 6.6880 | 0.0682 | 3.9723 | 0.0452 | 9.97 |
| 35000 | 402 | 106 | 6.6878 | 0.0682 | 3.9722 | 0.0452 | 9.97 |
| 40000 | 460 | 121 | 6.6877 | 0.0682 | 3.9721 | 0.0452 | 9.97 |
| 45000 | 517 | 137 | 6.6875 | 0.0682 | 3.9720 | 0.0452 | 9.97 |
| 50000 | 575 | 152 | 6.6879 | 0.0682 | 3.9722 | 0.0452 | 9.97 |
| 55000 | 632 | 167 | 6.6878 | 0.0682 | 3.9722 | 0.0452 | 9.97 |
| 60000 | 690 | 182 | 6.6877 | 0.0682 | 3.9721 | 0.0452 | 9.97 |
| 65000 | 747 | 197 | 6.6876 | 0.0682 | 3.9720 | 0.0452 | 9.97 |
| 70000 | 805 | 213 | 6.6878 | 0.0682 | 3.9722 | 0.0452 | 9.97 |
| 75000 | 862 | 228 | 6.6877 | 0.0682 | 3.9721 | 0.0452 | 9.97 |
| 80000 | 920 | 243 | 6.6877 | 0.0682 | 3.9721 | 0.0452 | 9.97 |
| 85000 | 977 | 258 | 6.6876 | 0.0682 | 3.9721 | 0.0452 | 9.97 |
| 90000 | 1035 | 273 | 6.6878 | 0.0682 | 3.9722 | 0.0452 | 9.97 |
| 95000 | 1092 | 289 | 6.6877 | 0.0682 | 3.9721 | 0.0452 | 9.97 |
| 100000 | 1150 | 304 | 6.6877 | 0.0682 | 3.9721 | 0.0452 | 9.97 |

As shown in Table 10 above, the composition of Example 5 comprises approximately 6.6% iron HEDTA (ounces of iron/total ounces), 0.07% micromate (ounces of micromate/total ounces), 0.07% glycerin (ounces of glycerin/total ounces), 3.97% urea (kilograms urea/total liters), 0.05% natural-based wetting agent (ounces of wetting agent/total ounces), and 9.97% MDS (gallons of MDS/total gallons). The composition may further comprise 0.07% glycerin (ounces of glycerin/total ounces) (not shown in Table 10).

Example 6

In another embodiment of the present disclosure, a kit is provided to kill weeds as well as fertilize plants, comprising iron hydroxyl ethylenediaminetriacetic acid, borresol humate HA-1, a chelated mix of micronutrients, feed grade urea, a natural-based wetting agent, and molasses desugarized solubles. The kit may contain micromate, a premixed composition of borresol humate HA-1 and chelated micronutrients. The kit may further comprise glycerin.

Example 7

In another embodiment of the present disclosure, the application of the composition to soil and plants in accordance with the teaching of the present disclosure kills weeds as well as fertilizes plants. The composition of the present disclosure is a post emergent weed control and fertilizer made from food grade ingredients that will kill most broad-leaf weeds without damaging the surrounding cultivated area. The ingredients in the composition of the present disclosure function as catalysts for oxygen reduction, which causes the production of unstable and highly reactive oxygen radicals, such as hydroxyl radicals. This causes cellular damage within the weed, leading to plant death. The weeds cannot handle the nutrient overload because they metabolize them too quickly causing them to die.

Figure 2A:
FIG. 2A is a photograph of a broad leaf weed 1 minute after application of the formulation of the present disclosure.
Figure 2B:
FIG. 2B is a photograph of the broad leaf weed shown in FIG. 2A 15 hours and 2 minutes after application of the formulation of the present disclosure.
Figure 2C:
FIG. 2C is a photograph of the broad leaf weed shown in FIG. 2A 21 hours and 50 minutes after application of the formulation of the present disclosure.
Figure 2D:
FIG. 2D is a photograph of the broad leaf weed shown in FIG. 2A 25 hours and 26 minutes after application of the formulation of the present disclosure.
Figure 2E:
FIG. 2E is a photograph of the broad leaf weed shown in FIG. 2A 42 hours and 12 minutes after application of the formulation of the present disclosure.
Figure 2F:
FIG. 2F is a photograph of the broad leaf weed shown in FIG. 2A 48 hours and 34 minutes after application of the formulation of the present disclosure.

Shown in FIGS. 2A-2F, application of the composition of the present disclosure was effective at killing a broadleaf weed. FIG. 2A shows the weed approximately one minute after application of the composition of the present disclosure. FIGS. 2B-2F shown the same weed at various time points after application. Weed death is evident approximately 2 days (48 hours) after application (FIG. 2F). The application of the composition of the present disclosure may be conducted in a variety of manners in order to allow the composition to kill weeds as well as fertilize surrounding plants. In the example shown in FIGS. 2A-2F, the composition of the present disclosure was applied evenly over the entire lawn area (blanket application, also known as surface broadcast) using a spray tank with a 2-gallon per minute cone gun nozzle. The composition was applied at a rate of 3 gallons per 1000 square feet. Other modes of application may be used, including but not limited to, injection, broadcast incorporated, band application, fertigation, foliar application, sidedress, topdress, and seed placement may be used.

Example 8

Figure 3A:
FIG. 3A is a photograph of a broad leaf weed 2 minutes after application of the formulation of the present disclosure.
Figure 3B:
FIG. 3B is a photograph of the broad leaf weed shown in FIG. 3A 18 hours and 36 minutes after application of the formulation of the present disclosure.
Figure 3C:
FIG. 3C is a photograph of the broad leaf weed shown in FIG. 3A 22 hours and 39 minutes after application of the formulation of the present disclosure.
Figure 3D:
FIG. 3D is a photograph of the broad leaf weed shown in FIG. 3A 25 hours and 54 minutes after application of the formulation of the present disclosure.
Figure 3E:
FIG. 3E is a photograph of the broad leaf weed shown in FIG. 3A 43 hours and 18 minutes after application of the formulation of the present disclosure.
Figure 3F:
FIG. 3F is a photograph of the broad leaf weed shown in FIG. 3A 47 hours and 49 minutes after application of the formulation of the present disclosure.
Figure 3G:
FIG. 3G is a photograph of the broad leaf weed shown in FIG. 3A 48 hours and 31 minutes after application of the formulation of the present disclosure.

Shown in FIGS. 3A-3F, application of the composition of the present disclosure was effective at killing a broadleaf weed while the surrounding grass remains unharmed and is fertilized by the composition. FIG. 3A shows the weed approximately two minutes after application of the composition of the present disclosure. FIGS. 3B-3G shown the same weed at various time points after application. Weed death is evident approximately 2 days (48 hours) after application (FIG. 3G). The application of the composition of the present disclosure may be conducted in a variety of manners in order to allow the composition to kill weeds as well as fertilize surrounding plants. In the example shown in FIGS. 3A-3G, the composition of the present disclosure was applied evenly over the entire lawn area (blanket application, also known as surface broadcast) using a spray tank with a 2-gallon per minute cone gun nozzle. The composition was applied at a rate of 3 gallons per 1000 square feet. Other modes of application may be used, including but not limited to, injection, broadcast incorporated, band application, fertigation, foliar application, sidedress, topdress, and seed placement may be used.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A composition for weed control and fertilizer comprising: iron hydroxyl ethylenediaminetriacetic acid, between 6.6% and 6.8% of the total volume, micromate, between 0.06% and 0.07% of the total volume, feed grade urea, between 3.90% (kg/L) and 4.05% (kg/L), a wetting agent, between 0.04% and 0.05% of the total volume, molasses desugarized solubles, between 6.5% and 10.5% of the total volume, and water, comprising the remainder portion of said composition.

2. The composition of claim 1 further comprising glycerin, wherein said glycerin is between 0.06% and 0.07% of the total volume.

3. A method for weed control and fertilization comprising the steps of:
   a. providing the composition of claim 1; and
   b. applying the composition to soil, lawn, or a cultivated area.

4. The method of claim 3, wherein said composition further comprises glycerin.

5. The method of claim 3, wherein an application amount is between 0.3 ounces and 0.4 ounces per square foot.

6. The method of claim 3, wherein said composition is applied to said soil, lawn, or a cultivated area by one or more of the following methods: injection, surface broadcast, broadcast incorporated, band application, fertigation, foliar application, sidedress, topdress, and seed placement.

7. The method of claim 3, further comprising the steps of: applying at least a second application of said composition to said soil, lawn, or a cultivated area.

8. The method of claim 7, wherein said composition further comprises glycerin.

9. The method of claim 7, wherein said composition is applied between 0.3 and 0.4 ounces per square foot.

10. The method of claim 7, wherein said composition is applied to said soil, lawn, or a cultivated area by one or more of the following methods: injection, surface broadcast, broadcast incorporated, band application, fertigation, foliar application, sidedress, topdress, and seed placement.

* * * * *